(12) United States Patent
Brockman et al.

(10) Patent No.: US 9,844,533 B2
(45) Date of Patent: Dec. 19, 2017

(54) ANTIOXIDANT-CONTAINING FOOD COMPOSITION FOR USE IN INHIBITING HISTAMINE PATHWAYS IN COMPANION ANIMALS

(75) Inventors: Jeffrey A. Brockman, Lawrence, KS (US); Steven C. Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 301 days.

(21) Appl. No.: 13/140,139

(22) PCT Filed: Dec. 16, 2009

(86) PCT No.: PCT/US2009/068236
§ 371 (c)(1),
(2), (4) Date: Jun. 16, 2011

(87) PCT Pub. No.: WO2010/077935
PCT Pub. Date: Jul. 8, 2010

(65) Prior Publication Data
US 2011/0251268 A1    Oct. 13, 2011

Related U.S. Application Data

(60) Provisional application No. 61/122,932, filed on Dec. 16, 2008.

(51) Int. Cl.
| | | |
|---|---|---|
| *A61K 31/385* | (2006.01) | |
| *A61P 39/06* | (2006.01) | |
| *A61P 29/00* | (2006.01) | |
| *A23K 20/158* | (2016.01) | |
| *A23K 50/40* | (2016.01) | |

(52) U.S. Cl.
CPC .......... *A61K 31/385* (2013.01); *A23K 20/158* (2016.05); *A23K 50/40* (2016.05)

(58) Field of Classification Search
None
See application file for complete search history.

(56) References Cited

U.S. PATENT DOCUMENTS

| 5,621,117 A | 4/1997 | Bethge et al. |
| 2009/0156658 A1 | 6/2009 | Zicker et al. |

FOREIGN PATENT DOCUMENTS

| JP | H07-556 | 7/1990 | |
| JP | 2012-511934 A | 5/2012 | |
| WO | WO 2006/058278 | 6/2005 | |
| WO | WO2007/002836 | * 1/2007 | |
| WO | WO2007/022344 | * 2/2007 | .......... A61K 31/375 |

OTHER PUBLICATIONS

Zicker et al. in Veterinary Therapeutics : Research in Applied Veterinary Medicine [2002, 3(2):167-176] (Abstract).*
Zicker et al. in Veterinary Therapeutics 3(2), 167-176 (2002).*
Little, S. Non-Obstructive Feline Urinary Tract Disease (Jun. 2001) in http://www.forestcats.net/index.php?option=com_content&view=article&id=117:non-obstructive-lower-urinary-tract-disease-in-the-cat&catid=4:articles&Itemid=70).*
Patuszka et al. in Medical Hypotheses 69(4), 957-958 (2007).*
Gill et al. in Journal of Clinical Pathology (1991); 44:243-235.*
Plotnick, A. in "Long-term Medical Managament of Feline Chronic Renal Failure" in web.archive.org/web/20081017233921/http://www.manhattancats.com/Articles/ CRF.html. (retrieved from the internet on Jun. 7, 2013).*
Mayer, R. discloses in Current Opinion in Infectious Diseases 20:77-82 (2007).*
Lundeberg et al. in British Journal of Urology 71, 427-429 (1993).*
Dru Forrester et al., Evidence-based management of feline lower urinary tract disease, The Veterinary Clinics of North America, Small Animal Practice 37:533-558 (2007).
International Search Report and the Written Opinion issued in International Application PCT/US2009/068236 dated Apr. 12, 2010.
Lamale et al., Interleukin-6 histamine, and methylhistamine as diagnostic markers for interstitial cystitis, Urology 68:702-706 (2006).
Rudick et al., Mast Cell-Derived Histamine Mediates Cystitis Pain, Journal of Urology 179:62 (2008).
Interstitial Cystitis, [online], archived on May 13, 2008, [searched on Nov. 29, 2013], Website <URL: https://web.archive.org/web/20080513045116/http://www.marvistavet.com/html/body_interstitial_cystitis.html.
Suzuki et al., 1994, "Analysis of significance of histamine for regulation of liver regeneration," Proceedings of Annual Conference of the Japan Society for Bioscience, Biotechnology and Agrochemistry, Japan 68(3):321.

* cited by examiner

*Primary Examiner* — Dennis Heyer

(57) ABSTRACT

The invention encompasses methods for inhibiting histamine release pathways in a companion animal, for example, felines and in treating or preventing idiopathic cystitis or interstitial cystitis. The compositions and methods of the invention include an amount of lipoic acid that is effective in inhibiting histamine release pathways in a companion animal, for example, felines and in treating or preventing idiopathic cystitis or interstitial cystitis.

6 Claims, No Drawings

ANTIOXIDANT-CONTAINING FOOD COMPOSITION FOR USE IN INHIBITING HISTAMINE PATHWAYS IN COMPANION ANIMALS

CROSS-REFERENCE TO RELATED APPLICATIONS

This application is a national stage entry under 35 U.S.C. §371 of International Patent Application No. PCT/US2009/068236, filed 16 Dec. 2009, which claims priority to U.S. Provisional Patent Application No. 61/122,932, which was filed 16 Dec. 2008, which is incorporated herein by reference in its entirety.

FIELD OF THE INVENTION

The invention encompasses methods for inhibiting histamine release pathways in a companion animal, for example, felines, and in treating or preventing idiopathic cystitis or interstitial cystitis. The methods of the invention include an amount of lipoic acid that is effective in inhibiting histamine release pathways in a companion animal, for example, felines, and in treating or preventing idiopathic cystitis or interstitial cystitis.

BACKGROUND OF THE INVENTION

It is believed that histamine and histamine release play a role in the etiology of interstitial cystitis in human females. Recent gene transcript profiling of cats with feline idiopathic cystitis (FIC) compared to the profiles of normal cats or cats with urinary tract infections indicate that genes involved in histamine release and signaling pathways are increased in expression in the cats with FIC. It is believed that histamine may also be involved in feline idiopathic cystitis. Similar gene transcript profiling of a panel of feline cell lines treated with or without lipoic acid indicate that lipoic acid decreases the expression of key genes in the same histamine release/signaling pathways that are up regulated in FIC. Feeding cats with lipoic acid may also reduce the symptoms or prevent the occurrence of FIC.

SUMMARY OF THE INVENTION

The invention encompasses methods of treating or preventing idiopathic cystitis in a companion animal, for example a feline or canine, including administering to a companion animal in need thereof a food composition comprising an effective amount of one or more antioxidants, for example, lipoic acid.

Another embodiment encompasses methods of treating or preventing interstitial cystitis in a companion animal, for example a feline or canine, including administering to a companion animal in need thereof a food composition comprising an effective amount of one or more antioxidants, for example, lipoic acid.

In all of these methods, it is desirable to administer the antioxidant or mixture thereof in the diet of the animal.

DETAILED DESCRIPTION OF THE INVENTION

General Description

The invention encompasses methods of inhibiting histamine related pathways in a companion animal comprising administering to a companion animal a food composition comprising an effective amount of lipoic acid to inhibit histamine related pathways in a companion animal, wherein said effective amount of lipoic acid to inhibit histamine related pathways in a companion animal is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the companion animal is a dog.

In certain embodiments, the companion animal is a cat.

In certain embodiments, the effective amount is effective to treat or prevent idiopathic cystitis or interstitial cystitis in a companion animal.

In certain embodiments, the pet food composition comprising lipoic acid is administered at least 15 days.

In certain embodiments, the pet food composition comprising lipoic acid is administered at least 30 days.

In certain embodiments, the pet food composition comprising lipoic acid is administered at least 45 days.

In certain embodiments, the pet food composition comprising lipoic acid is administered daily.

In another embodiment, the invention encompasses methods of treating idiopathic cystitis or interstitial cystitis in a companion animal comprising administering to a companion animal in need thereof a food composition comprising an effective amount of lipoic acid, wherein said effective amount of lipoic acid is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the companion animal is a dog.

In certain embodiments, the companion animal is a cat.

In certain embodiments, the pet food composition comprising lipoic acid is administered at least 15 days.

In certain embodiments, the pet food composition comprising lipoic acid is administered at least 30 days.

In certain embodiments, the pet food composition comprising lipoic acid is administered at least 45 days.

In certain embodiments, the pet food composition comprising lipoic acid is administered daily.

The diet fed to the adult companion pet, for example canine and feline, is the standard normal diet fed to an animal of that age. Below is a typical diet for a canine of 1 to 6 years of age.

TABLE 1

| Component | Amount (wt. % of dry matter) |
|---|---|
| Protein | 0-95% |
| Fat | 0-50% |
| carbohydrate | 0-75% |

The inventors have also surprisingly found that the addition of one or more antioxidants, for example lipoic acid, to an animal food is useful in inhibiting histamine related pathway in companion animals, for example, dogs and cats.

As used herein, the term "inhibiting histamine related pathway" refers to the ability of a companion animals to have reduced release of histamine and thereby treat or prevent disorders associated with histamine release. Accordingly, a companion animal, for example, a dog or cat, eating a pet food containing an antioxidant, for example, lipoic acid, will have inhibited histamine related pathway (e.g., gene networks) and therefore will be less susceptible to diseases and disorders associated with histamine release, for example, idiopathic cystitis or interstitial cystitis and will overcome a disease or disorder associated with histamine release faster than an animal not consuming antioxidants, for example, lipoic acid.

The component in the diet, which accomplishes this, is an antioxidant or mixture thereof. An antioxidant is a material that quenches a free radical. Examples of such materials include foods such as ginkgo biloba, citrus pulp, grape pomace, tomato pomace, carrot and spinach, all preferably dried, as well as various other materials such as beta-carotene, selenium, coenzyme Q10 (ubiquinone), lutein, tocotrienols, soy isoflavones, S-adenosylmethionine, glutathione, taurine, N-acetylcysteine, vitamin E, vitamin C, alpha-lipoic acid, L-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The D form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like, which will function in a vitamin C like activity after ingesting by the pet. They can be in any form such as liquid, semisolid, solid and heat stable form. Alpha-lipoic acid can be administered into the diet as alpha-lipoic acid or as a lipoate derivative as in U.S. Pat. No. 5,621,117, racemic mixtures, salts, esters or amides thereof. L-carnitine can be administered in the diet and various derivatives of carnitine such as the salts such as the hydrochloride, fumarate and succinates, as well as acetylated carnitine and the like, can be used.

The quantities administered in the diet, all as wt % (dry matter basis) of the diet, are calculated as the active material, per se, that is measured as free material. The maximum amounts employed should not bring about toxicity.

At least about 100 ppm or at least about 150 ppm of vitamin can be used. In certain embodiments, the range of about 500 to about 1,000 ppm can be employed. Although not necessary a maximum of about 2,000 ppm or about 1,500 ppm is generally not exceeded.

With respect to vitamin C at least about 50 ppm is used, desirably at least about 75 ppm and more desirably at least about 100 ppm. A nontoxic maximum can be employed.

The quantity of alpha-lipoic acid can vary from at least about 25 ppm, desirably at least about 50 ppm, more desirably about 100 ppm. In various embodiments, the range of lipoic acid that can be administered to dogs is about 150 ppm to about 4500 ppm. In various embodiments, the range of lipoic acid that can be administered to cats is about 65 ppm to about 2600 ppm. Maximum quantities can vary from about 100 ppm to an amount which remains nontoxic to the pet. In certain embodiments, a range is from about 100 ppm to about 200 ppm.

For L-carnitine about 50 ppm, desirably about 200 ppm, more desirably about 300 ppm for canines are a useful minimum. For felines, slightly higher minimums of L-carnitine can be employed such as about 100 ppm, 200 ppm, and 500 ppm. A nontoxic maximum quantity can be employed, for example, less than about 5,000 ppm. For canines, lower quantities can be employed, for example, less than about 5,000 ppm. For canines a preferred range is about 200 ppm to about 400 ppm. For felines a preferred range is about 400 ppm to about 600 ppm.

Beta-carotene at about 1-15 ppm can be employed.
Selenium at about 0.1 up to about 5 ppm can be employed.
Lutein: at least about 5 pm can be employed.
Tocotrienols: at least about 5 ppm can be employed.
Coenzyme Q10: at least about 25 ppm can be employed.
S-adenosylmethionine: at least about 50 ppm can be employed.
Taurine: at least about 1000 ppm can be employed.
Soy isoflavones: at least about 25 ppm can be used.
N-acetylcysteine: at least about 50 ppm can be used.
Glutathione: at least about 50 ppm can be used.
Gingko biloba: at least 50 ppm of extract can be used.

The following are raw ingredients that are high in ORAC (Oxygen radical absorbing capacity) content: Spinach pomace, Tomato pomace, Citrus pulp, Grape pomace, Carrot granules, Broccoli, Green tea, Ginkgo biloba and Corn gluten meal. When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content>25 µmole of Trolox equivalents per gram of dry matter could be used if added at 1% in combination with four other 1% ingredients for a total of 5% addition to the diet.

EXAMPLES

Example 1

It was an unexpected finding that lipoic acid down regulates the same histamine release and signaling pathways (gene networks) that are up regulated in Feline idiopathic Cystitis. Adding lipoic acid to a cat's diet may treat and or prevent FIC.

Whole blood samples were collected from cats with feline idiopathic cystitis (x), cats with urinary tract infections, or normal cats in Paxgene tubes. Total RNAs were isolated from whole blood samples using the PAXgene RNA isolation kit. All measurements were done with the Hill's feline-2 Affymetrix genechips. For statistical analysis, all measurements were normalized with RMA. All analysis was preformed using Partek. An ANOVA t-test was performed for genes that are differentially expressed between normal and cats with either feline idiopathic cystitis or urinary tract infections.

Differentially expressed genes between normal cats vs. cats with feline idiopathic cystitis and normal cats vs. cats with urinary tract infection (UTI) were analyzed. Genes that showed at least a 20% average change between groups with a p value of <0.05 were selected. The gene list was uploaded into the GeneGo analysis program where 529 changed by FIC were recognized by the program and 608 changed by UTI were recognized.

Each gene set was analyzed for enrichment in particular pathways or gene networks. Under the drug target network function of the program it was identified that multiple Histamine release and signaling pathways were affected by FIC but not UTI.

The Histamine signaling pathway was up regulated in FIC.

TABLE 2

Histamine Signaling Pathway

| Number | Gene Symbol | Protein | Protein Name | Feline Control v. FIC Signal | p-value |
|---|---|---|---|---|---|
| 1 | ADCY4 | ADCY4 Human | Adenylate Cyclase Type 4 | 0.3646 | 0.03318 |
| 2 | MAPK1 | MK01 Human | Mitogen-activated Protein Kinase 1 | 0.2856 | 0.03422 |
| 3 | PRDX6 | PRDX6 Human | Peroxiredoxin-6 | 0.2231 | 0.04389 |

The IgE signaling pathway which triggers the release of histamine is up regulated in FIC.

TABLE 3

IgE Signaling Pathway

| Number | Gene Symbol | Protein | Protein Name | Feline Control v. FIC Signal | p-value |
|---|---|---|---|---|---|
| 1 | ALOX5 | LOX5_HUMAN | Arachidonate 5-lipoxygenase | 0.2311 | 0.04739 |
| 2 | GAB2 | GAB2_HUMAN | GRB2-associated-binding protein 2 | 0.2151 | 0.00489 |
| 3 | LYN | LYN_HUMAN | Tyrosine-protein kinase Lyn | 0.1823 | 0.0008876 |
| 4 | MAPK1 | MK01_HUMA | Mitogen-activated protein kinase 1 | 0.2852 | 0.03422 |

Example 2

The gene expression data from four cat cell lines treated with lipoic acid was analyzed. All four cell lines with or without lipoic acid were analyzed by a paired t test and all genes that showed a statistical significance of less than 0.05 were up loaded into GeneGo for enrichment analysis. Key genes in the networks listed above were down regulated by lipoic acid.

TABLE 4

FIC Cells

| Number | Gene Symbol | Protein | Protein Name | Feline Control v. FIC Signal | p-value |
|---|---|---|---|---|---|
| 1 | GAB2 | GAB2_HUMAN | GRB2-associated-binding protein 2 | −0.8668 | 0.02305 |
| 2 | LTC4S | LTC4S_HUMAN | Leukotriene C4 synthase | −0.4586 | 0.03719 |
| 3 | MAP2K1 | MP2K1_HUMAN | Dual specificity mitogen-activated protein kinase 1 | −0.1574 | 0.03509 |
| 4 | MAPK1 | MK01_HUMAN | Mitogen-activated protein kinase 1 | −0.3117 | 0.0193 |

TABLE 5

FIC CATS

| Number | Gene Symbol | Protein | Protein Name | Feline Control v. FIC Signal | p-value |
|---|---|---|---|---|---|
| 1 | ADCY2 | ADCY_HUMAN | Adenylate cyclase type 2 | 0.3925 | 0.01807 |
| 2 | ADCY7 | ADCY7_HUMAN | Adenylate cyclase type 7 | 0.3988 | 0.0393 |
| 3 | MAPK1 | MK01_HUMAN | Mitogen-activated protein kinase 1 | −0.3117 | 0.0193 |
| 4 | NOS3 | NOS3_HUMAN | Nitric oxide synthase, endothelial | −0.5503 | 0.009156 |

TABLE 5-continued

FIC CATS

| Number | Gene Symbol | Protein | Protein Name | Feline Control v. FIC Signal | p-value |
|---|---|---|---|---|---|
| 5 | PLA2G2F | PA2GF_HUMAN | Group IIFA2 secretory phospholipase precursor | 1.061 | 0.03852 |
| 6 | PNPLA8 | PLPL8_HUMAN | Calcium-independent phospholipase A2-gamma | −0.2652 | 0.006656 |
| 7 | PRKAR1A | KAP0_HUMAN | cAMP-dependent protein kinase type I-alpha regulatory subunit | −0.184 | 0.03069 |
| 8 | REL | REL_HUMAN | C-Rel proto-oncogene protein | −0.4264 | 0.01856 |
| 9 | RELA | TF65_HUMAN | Transcription factor p65 | −0.429 | 0.002904 |
| 10 | TNF | TNFA_HUMAN | Tumor necrosis factor precursor | 0.1797 | 0.04854 |
| 11 | VCAM1 | VCAM1_HUMAN | Vascular cell adhesion protein 1 precursor | −0.7819 | 0.004064 |

Based on the illustrative embodiments of the invention, it was surprisingly found that lipoic acid may be able to block the downstream activation of pathways that lead to the release of and biological function of histamine. Therefore, lipoic acid may be useful in the treatment and/or prevention of feline idiopathic cystitis.

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A method of inhibiting histamine related pathways in a companion animal comprising
administering to a companion animal in need thereof a food composition comprising
a mixture of antioxidants comprising taurine and an effective amount of lipoic acid to inhibit histamine related pathways in the companion animal,
wherein the effective amount of lipoic acid to inhibit histamine related pathways in the companion animal comprises about 600 ppm to 2600 ppm of lipoic acid,
wherein the companion animal is a cat suffering from interstitial cystitis or idiopathic cystitis,
wherein the effective amount is effective to treat idiopathic cystitis or interstitial cystitis in the cat, and
wherein the mixture of antioxidants further comprises L-carnitine in an amount of 500 ppm to about 5,000 ppm.

2. The method of claim 1, wherein the pet food composition comprising lipoic acid is administered for at least 15 days.

3. The method of claim 1, wherein the pet food composition comprising lipoic acid is administered for at least 30 days.

4. The method of claim 1, wherein the pet food composition comprising lipoic acid is administered for at least 15 days up to 45 days.

5. The method of claim 1, wherein the pet food composition comprising lipoic acid is administered daily.

6. The method of claim 1, wherein the mixture of antioxidants comprises taurine in an amount of at least 1000 ppm.

* * * * *